US012685823B2

(12) United States Patent
Yu et al.

(10) Patent No.: US 12,685,823 B2
(45) Date of Patent: Jul. 21, 2026

(54) MEDICAMENT FILLING SYSTEM

(71) Applicant: Becton, Dickinson and Company, Franklin Lakes, NJ (US)

(72) Inventors: Bo Yang Yu, Winchester, MA (US); Bradley Wilkinson, North Haledon, NJ (US); Bart Peterson, Farmington, UT (US); Mark Newby, Kamas, UT (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 1149 days.

(21) Appl. No.: 17/764,495

(22) PCT Filed: Sep. 25, 2020

(86) PCT No.: PCT/US2020/052760
§ 371 (c)(1),
(2) Date: Mar. 28, 2022

(87) PCT Pub. No.: WO2021/067134
PCT Pub. Date: Apr. 8, 2021

(65) Prior Publication Data
US 2022/0339365 A1      Oct. 27, 2022

Related U.S. Application Data

(60) Provisional application No. 62/908,377, filed on Sep. 30, 2019.

(51) Int. Cl.
A61M 5/315 (2006.01)
A61M 5/178 (2006.01)
(Continued)

(52) U.S. Cl.
CPC ...... A61M 5/31553 (2013.01); A61M 5/1782 (2013.01); A61M 39/223 (2013.01); A61M 39/24 (2013.01); A61M 5/3202 (2013.01)

(58) Field of Classification Search
CPC ............ A61M 5/31553; A61M 5/1782; A61M 5/3202; A61M 5/31528; A61M 5/3155; (Continued)

(56) References Cited

U.S. PATENT DOCUMENTS

| | | | |
|---|---|---|---|
| 4,498,904 A | 2/1985 | Turner et al. | |
| 5,246,011 A | 9/1993 | Caillouette | |

(Continued)

FOREIGN PATENT DOCUMENTS

| | | |
|---|---|---|
| JP | 2012525868 A | 10/2012 |
| WO | 2019023252 A1 | 1/2019 |

OTHER PUBLICATIONS

CN Application No. 202011029489.7, Office Action issued Aug. 9, 2025, and English translation.

(Continued)

*Primary Examiner* — Tasnim Mehjabin Ahmed
(74) *Attorney, Agent, or Firm* — Dickinson Wright, PLLC

(57) ABSTRACT

A syringe assembly (2) that locks a syringe (10) to prevent backflow of medicament, the syringe assembly (2) comprising a syringe (10) including a barrel (12) configured to carry the medicament, a plunger (14) that communicates with the barrel (12), and a plunger head (16) disposed on a proximal end of the plunger (14), and a locking assembly (50) disposed around the barrel (12), wherein the locking assembly (50) prevents the plunger (14) from moving away from the barrel (12) to draw the medicament into the barrel (12).

12 Claims, 15 Drawing Sheets

(51) Int. Cl.
    *A61M 39/22*     (2006.01)
    *A61M 39/24*     (2006.01)
    *A61M 5/32*     (2006.01)

(58) Field of Classification Search
    CPC .............. A61M 5/3293; A61M 5/3298; A61M
               5/31505; A61M 39/223; A61M 39/24;
                        A61M 2205/582
    See application file for complete search history.

(56)                    References Cited

U.S. PATENT DOCUMENTS

| | | | | |
|---|---|---|---|---|
| 5,356,395 | A | * | 10/1994 | Chen ................... A61M 5/3213 |
| | | | | 604/263 |
| 5,637,092 | A | * | 6/1997 | Shaw ................. A61M 5/5013 |
| | | | | 604/110 |
| 5,830,152 | A | | 11/1998 | Tao |
| 8,062,254 | B2 | | 11/2011 | Maclean |
| 2003/0105430 | A1 | | 6/2003 | Lavi et al. |
| 2010/0084041 | A1 | | 4/2010 | Fehr et al. |
| 2010/0276034 | A1 | | 11/2010 | Gonnelli et al. |
| 2014/0018770 | A1 | | 1/2014 | Sutkin |
| 2019/0060576 | A1 | | 2/2019 | Kwolek et al. |
| 2022/0362106 | A1 | * | 11/2022 | Gyory ................... A61J 1/2037 |

OTHER PUBLICATIONS

Canadian Patent Application No. 3,151,405, Office Action issued Jan. 13, 2026.

* cited by examiner

DRAW

EJECT

MEDICAMENT FILLING SYSTEM

RELATED APPLICATION

This application claims the benefit under 35 U.S.C. § 119(e) of U.S. Provisional Patent Application Ser. 62/908, 377, filed on Sep. 30, 2019, which is hereby incorporated by reference in its entirety.

FIELD OF THE INVENTION

Various exemplary embodiments of the invention relate to devices that fill a delivery device with medicament.

BACKGROUND OF THE INVENTION

Systems such as delivery devices and syringe assemblies are typically used to inject medication, such as insulin, into a patient. However, inefficiencies and inconveniences can arise. These challenges include providing dosage feedback, minimizing air entering into the delivery device, preventing medicament backflow from exiting the delivery device during and after the filling step, and improving safety, handling and stability.

SUMMARY OF THE INVENTION

It is an aspect of the present invention to provide a syringe assembly that locks a syringe to prevent backflow of medicament. After the delivery device is filled with the medicament, a plunger of the syringe is configured to prevent medicament backflow from the delivery device into the syringe. Such an assembly provides efficient and improved accuracy of the medicament transferred to the delivery device.

Another aspect of the present invention provides a syringe assembly that provides haptic feedback during dose setting. Such a configuration gives a user confirmation of a specified dose setting, prevents unintended locking and minimizes user confusion.

In another aspect of the present invention, a fluid transfer device engages a syringe to provide different fluid paths for drawing medicament and injecting the medicament. Such a configuration prevents medicament backflow from the delivery device into the syringe, avoids the use of a locking mechanism and provides efficient and improved accuracy of the medicament transferred to the delivery device while not modifying the syringe.

The foregoing and/or other aspects of the present invention can be achieved by providing a syringe assembly that locks the syringe to prevent backflow of medicament, the syringe assembly comprising a syringe including a barrel configured to carry the medicament, a plunger that communicates with the barrel, and a plunger head disposed on a proximal end of the plunger, and a locking assembly disposed around the barrel, wherein the locking assembly prevents the plunger from moving away from the barrel to draw the medicament into the barrel.

The foregoing and/or other aspects of the present invention can further be achieved by providing a syringe assembly that provides haptic feedback during dose setting, the syringe assembly comprising a syringe including a barrel configured to carry a medicament, a plunger having a plunger head disposed on a proximal end of the plunger, the plunger communicating with the barrel, the plunger including a plurality of axial ribs extending along a length of the plunger, and a notch disposed in each axial rib, and a dose selector disposed around the barrel, wherein the dose selector passes through one of the notches to set a dose.

The foregoing and/or other aspects of the present invention can also be achieved by providing a fluid transfer device that prevents backflow of medicament, the fluid transfer device comprising a barrel configured to carry the medicament, a plunger connected to the barrel, and a vial adapter comprising a first needle cannula that allows the medicament to exit the fluid transfer device, a second needle cannula that allows the medicament to enter the fluid transfer device, the second needle cannula being shorter in length than the first needle cannula, a first one-way valve connected to the first needle cannula, and a second one-way valve connected to the second needle cannula.

The foregoing and/or other aspects of the present invention can additionally be achieved by providing a fluid transfer device that prevents backflow of medicament, the fluid transfer device comprising a first needle cannula that allows the medicament to exit the fluid transfer device, a second needle cannula that allows the medicament to enter the fluid transfer device, the second needle cannula being shorter in length than the first needle cannula, the second needle cannula being disposed within the first needle cannula, and a two-way valve connected to the first needle cannula and the second needle cannula, wherein the second needle cannula is configured to draw the medicament from a vial, and when the fluid transfer device is engaged to a delivery device, the first needle cannula transfers medicament to the delivery device.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
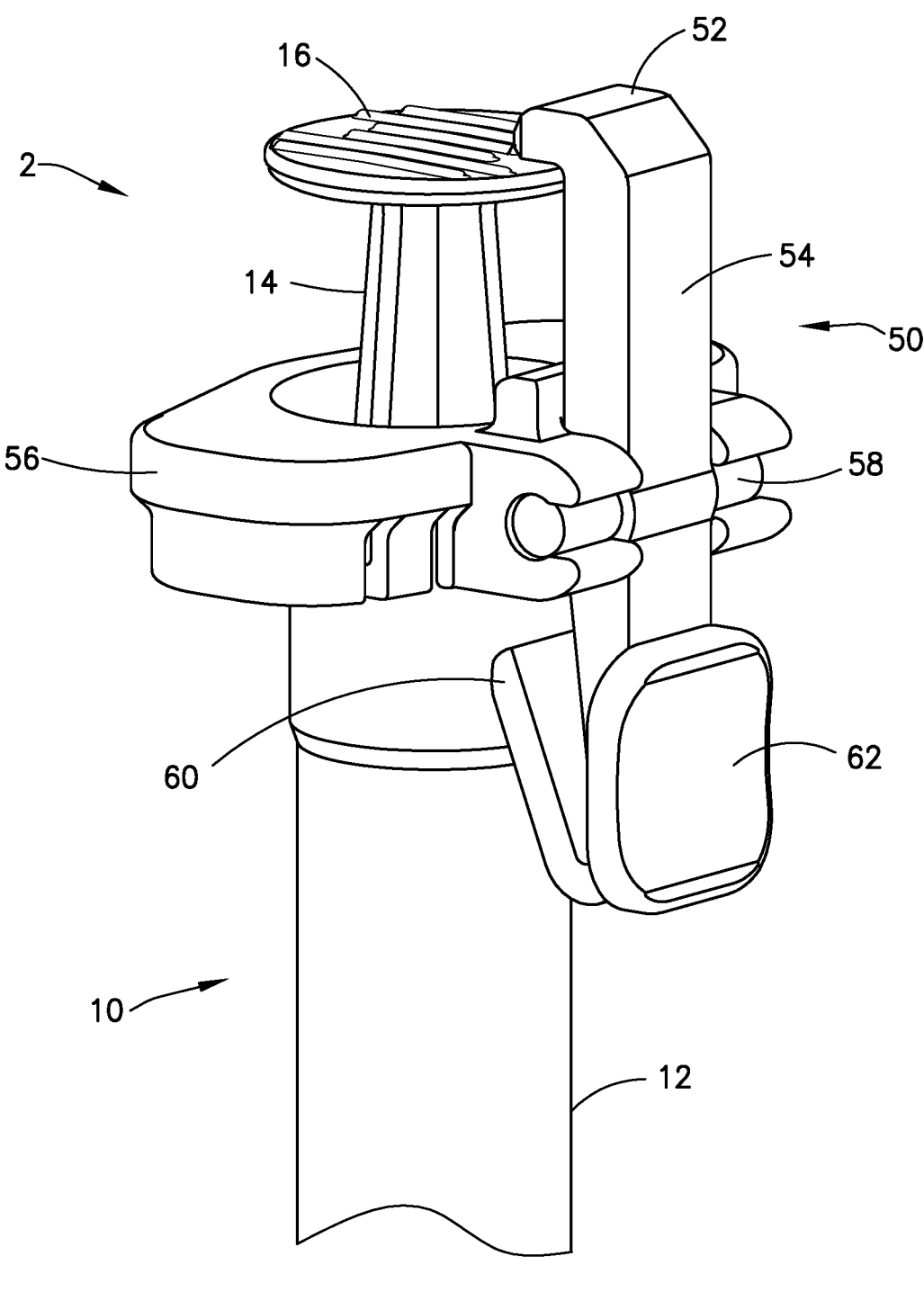
FIG. 1 illustrates a first exemplary embodiment of a left perspective view of a syringe assembly.

FIG. 1 illustrates a syringe assembly 2 according to one embodiment. The syringe assembly 2 includes a syringe 10 having a barrel 12, a plunger 14, a plunger head 16 and a needle (not shown) as conventionally understood by one skilled in the art. Specifically, the barrel 12 carries medicament and the plunger 14 is disposed in the barrel 12 to move the medicament into and out of the barrel 12. The plunger head 16 is connected to a proximal end of the plunger 14 and allows a user to move the plunger 14 to perform the medicament filling and dispensing operations. The needle receives the medicament from a vial and dispenses the medicament to an insulin delivery device.

The syringe assembly 2 further includes a locking assembly 50 that locks the plunger 14 of the syringe 10 after the medicament is dispensed to advantageously prevent backflow of medicament into the barrel 12. The locking assembly 50 includes a hook 52, an arm 54, a base 56, a pivot shaft 58, a spring member 60 and a button 62.

The hook 52 is disposed on a proximal end of the arm 54 and includes a cantilevered surface that is configured to engage a top surface of the plunger head 16 when the medicament is dispensed from the barrel 12 of the syringe 10. The base 56 is fixed to the barrel 12 and surrounds barrel 12. The pivot shaft 58 is disposed on a side surface of the base 56 and is rotatable. The pivot shaft 58 engages a central portion of the arm 54 to allow the hook 52 to rotate.

A distal end of the arm 54 includes the spring member 60 and the button 62. The spring member 60 contacts the barrel 12 at one side of the arm 54 and the button 62 is disposed on an opposing side of the arm 54 to provide the user with a depressible surface. The hook 52 is configured to rotate about the pivot shaft 58 disposed between the button 62 and the hook 52. The pivot shaft 58 allows the arm 54 to rotate between an engaged and a disengaged position based on user activation of the button 62.

Specifically, when the medicament from the syringe 10 is dispensed, the plunger 14 is at a distal position. A natural state of the locking assembly 50 positions the hook 52 above the plunger head 16 to lock the plunger 14 from movement. In this state, the button 62 is in a free or released state and the spring member 60 pushes the button 62 (a first compression force) to provide maximum engagement of the hook 52 to the plunger head 16.

To unlock the syringe 10 from the locking assembly 50, the user depresses the button 62 against the springe force of the spring member 60 (a second compression force). This causes the arm 54 to rotate about the pivot shaft 58 and disengage the hook 52 from the plunger head 16. The second compression force is greater than the first compression force.

When a syringe conventionally fills an insulin delivery device, the user must simultaneously hold down the plunger head and remove the syringe from the insulin delivery device to avoid backflow of medicament into the syringe 10. The locking assembly 50 disclosed herein advantageously locks the plunger head 16 after the medication is dispensed into the insulin delivery device. In this manner, no medicament will backflow into the syringe 10 and the user can comfortably remove the syringe 10 from the insulin delivery device. The locking assembly 50 also advantageously allows the user to unlock the syringe 10 for use if the syringe 10 was accidentally locked.

Figure 2:
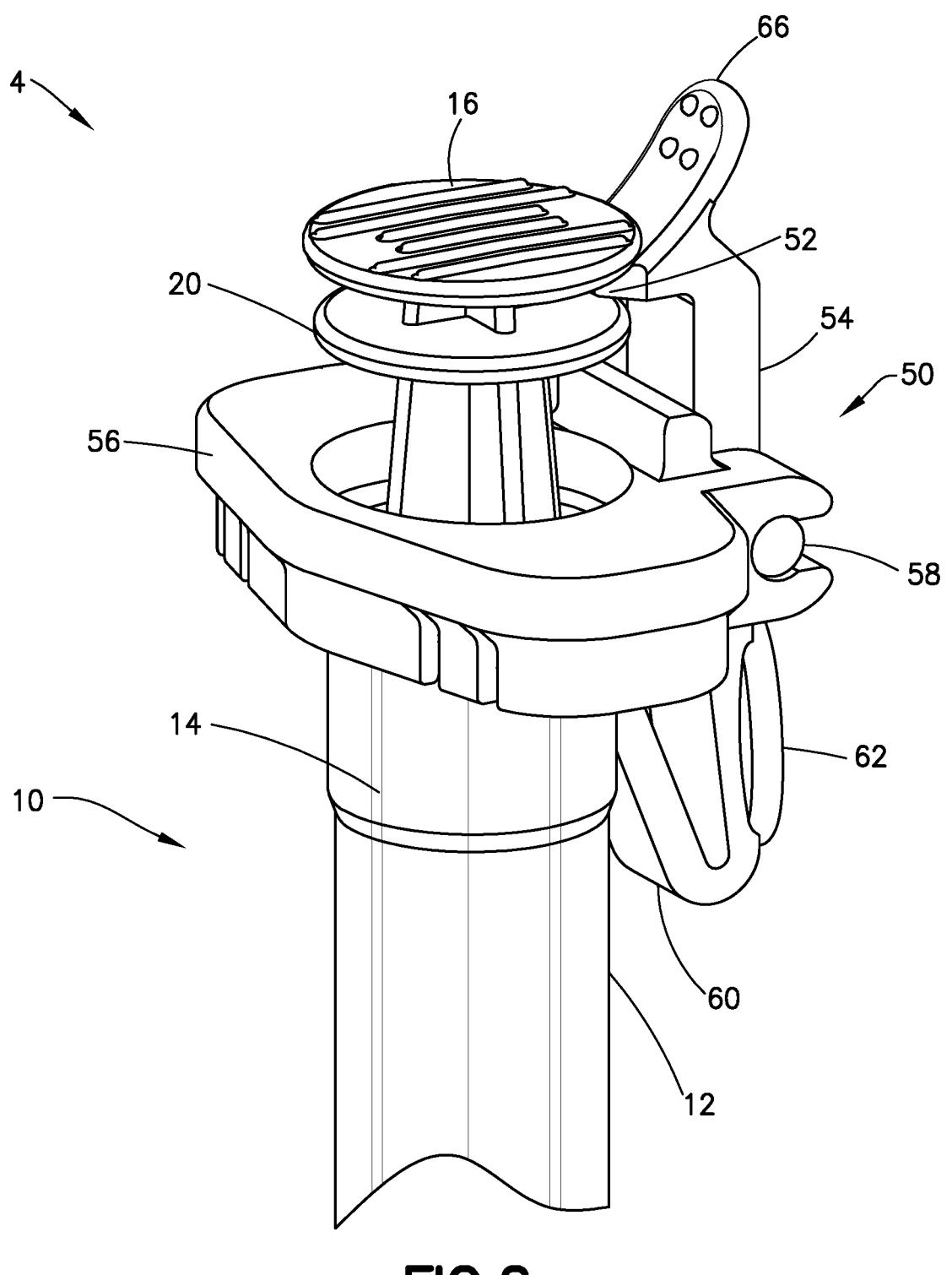
FIG. 2 illustrates a second exemplary embodiment of a right perspective view of a syringe assembly with a plunger head platform.

FIG. 2 illustrates a syringe assembly 4 according to a second embodiment. This embodiment discloses the syringe 10 and the locking assembly 50 as similarly described above with the following modifications. The plunger head 16 of the syringe 10 includes a plunger head platform 20. The platform 20 is disposed below the plunger head 16 such that a gap is present between the two features. The platform 20 is preferably molded as part of the plunger 14 but alternately can be a separate part attached to the plunger 14. The hook 52 of the locking assembly 50 is advantageously configured to engage the gap to lock the plunger 14 after the medicament is dispensed from the barrel 12 of the syringe 10.

Additionally, the hook 52 includes a plurality of protrusions 66 that provide a depressible surface. Accordingly, the user can advantageously apply a force to the hook 52 where the plurality of protrusions 66 are located or apply a force to the button 62 to move the hook 52 from an engaged, locked position to a disengaged, unlocked position. The configuration in this embodiment advantageously provides a complete surface at the plunger head 16 available for the user to manipulate when engaging and disengaging the locking assembly 50.

Figure 3:
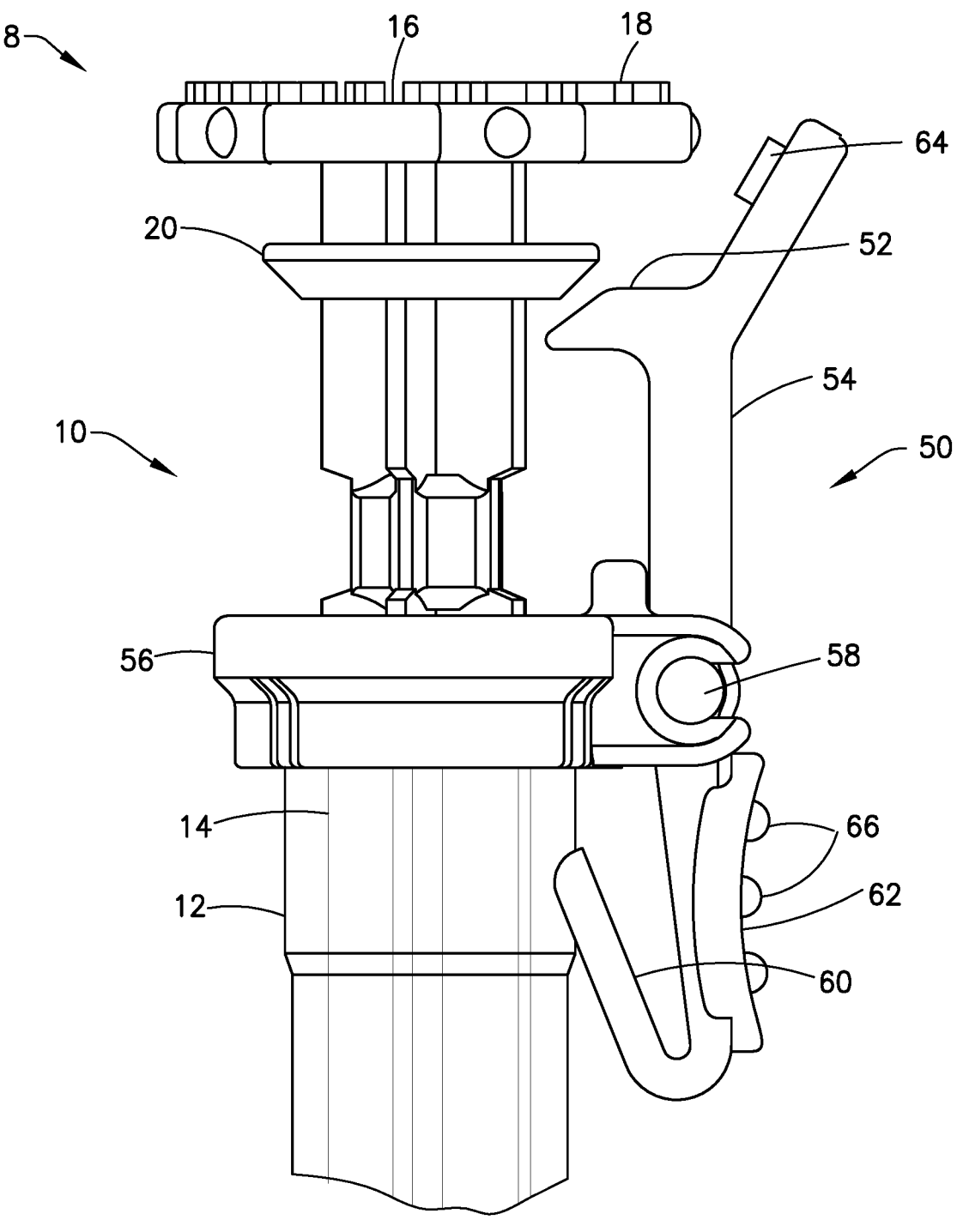
FIG. 3 illustrates a third exemplary embodiment of aside elevation view of a syringe assembly with a dial dose and a position indicator.
Figure 4:
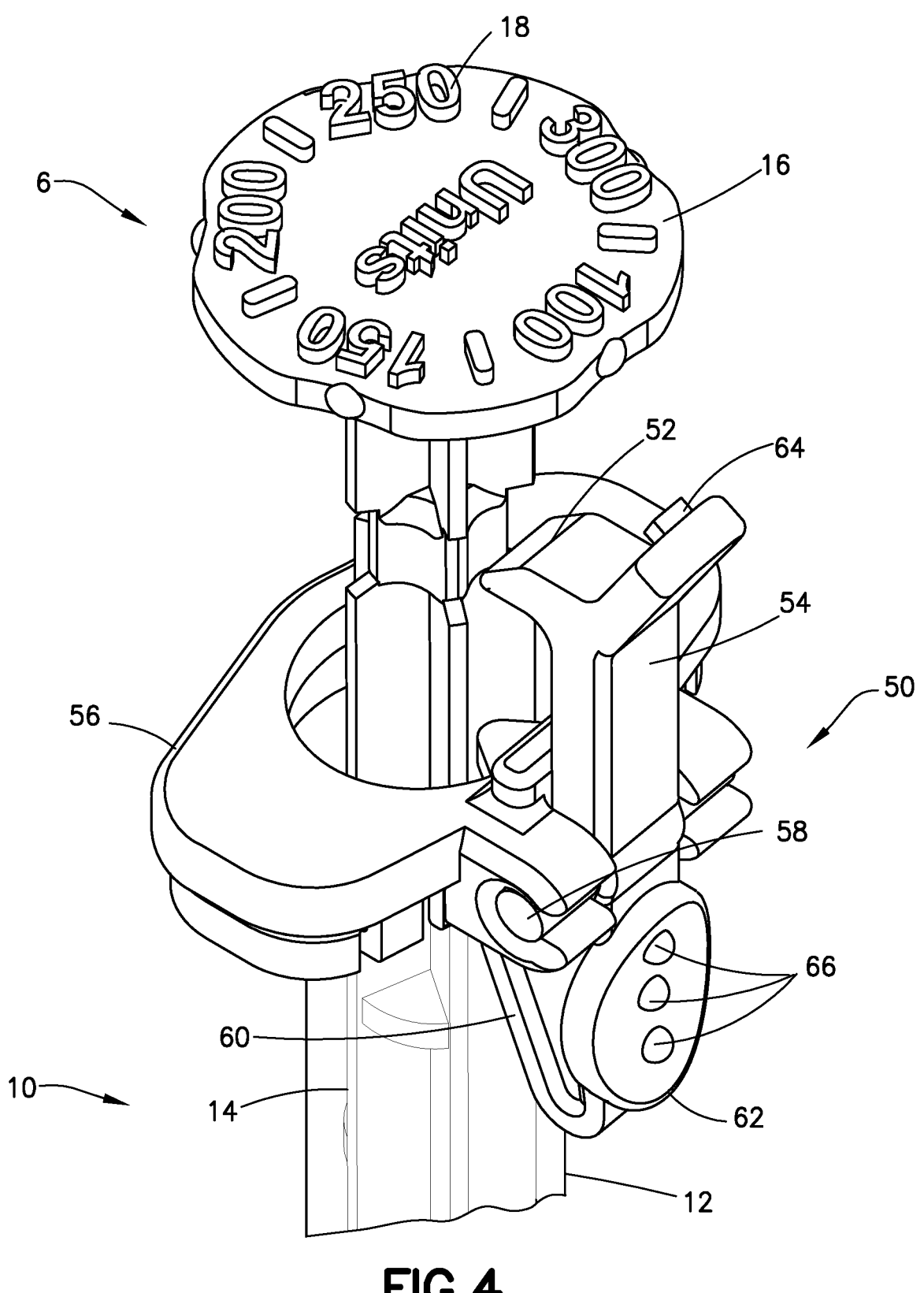
FIG. 4 is a perspective view of the syringe assembly of FIG. 3 in an unlocked position.
Figure 5:
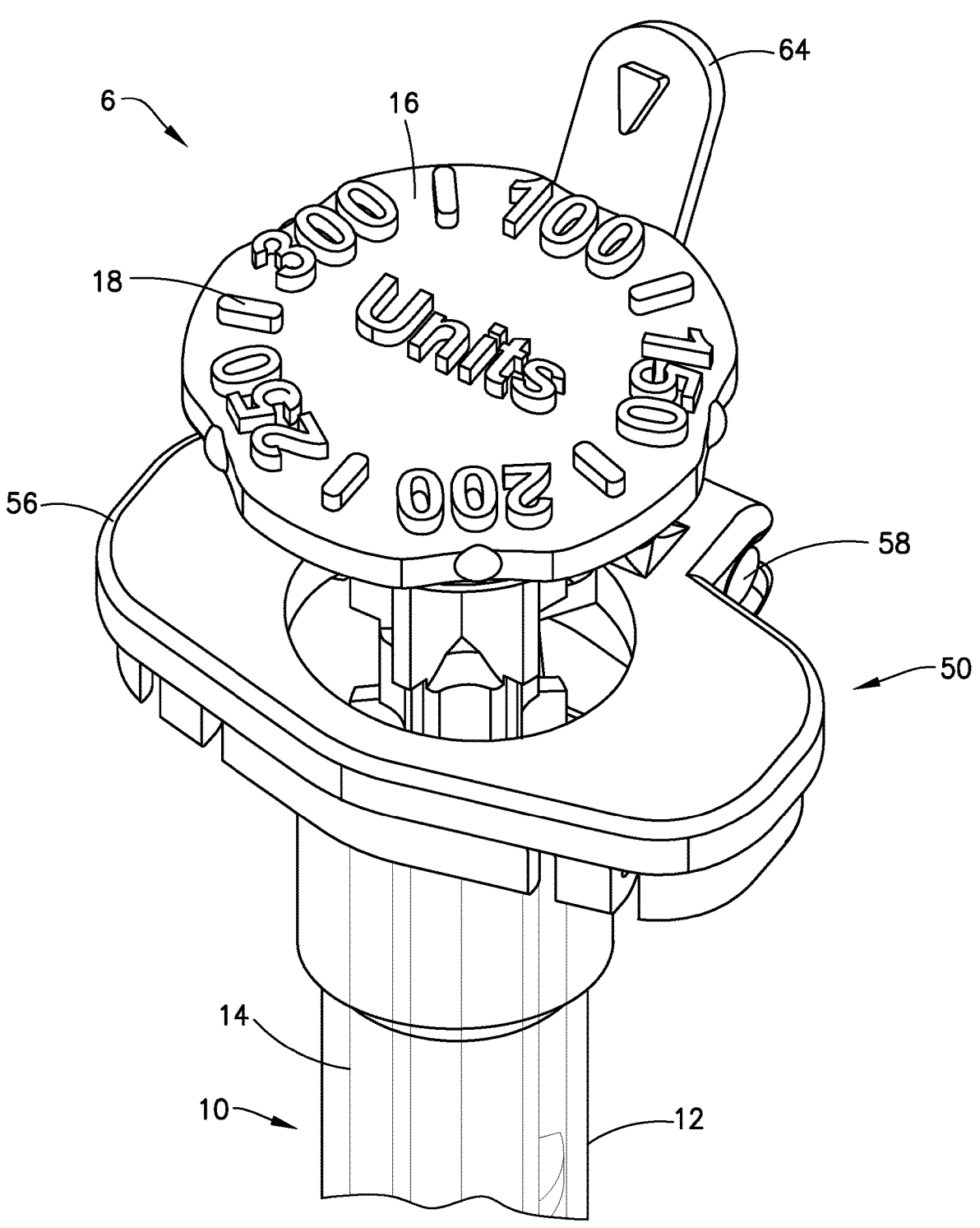
FIG. 5 is a perspective view of the syringe assembly of FIG. 3 in a locked position.

FIGS. 3-5 illustrate a syringe assembly 6 according to a third embodiment. This embodiment discloses the syringe 10 and the locking assembly 50 as similarly described above with the following modifications. The plunger head 16 includes a dial dose 18. The dial dose 18 indicates a dosage unit amount. Specifically, the plunger head 16 is rotated to set a desired dose identified by the dial dose 18.

In addition, the locking assembly 50 includes a position indicator 64 shaped as an arrowhead. The position indicator 64 advantageously cooperates with the dial dose 18 to identify a dose position of the plunger head 16. As illustrated in FIG. 5, the position indicator 64 points to a specific dosage amount expressed by the dial dose 18 that is set by the user via rotation of the plunger head 16. The button 62 on the locking assembly 50 also includes protrusions 66 that provide a friction surface for the user to depress the button 62.

In operation, FIGS. 3 and 4 illustrate an unlocked position of the locking assembly 50 whereas FIG. 5 illustrates a locked position. In the unlocked position, the plunger 14 is free to move in the barrel. In the locked positon, the plunger 14 is unable to move since the hook 52 engages the platform 20 to prevent movement.

Figure 6:
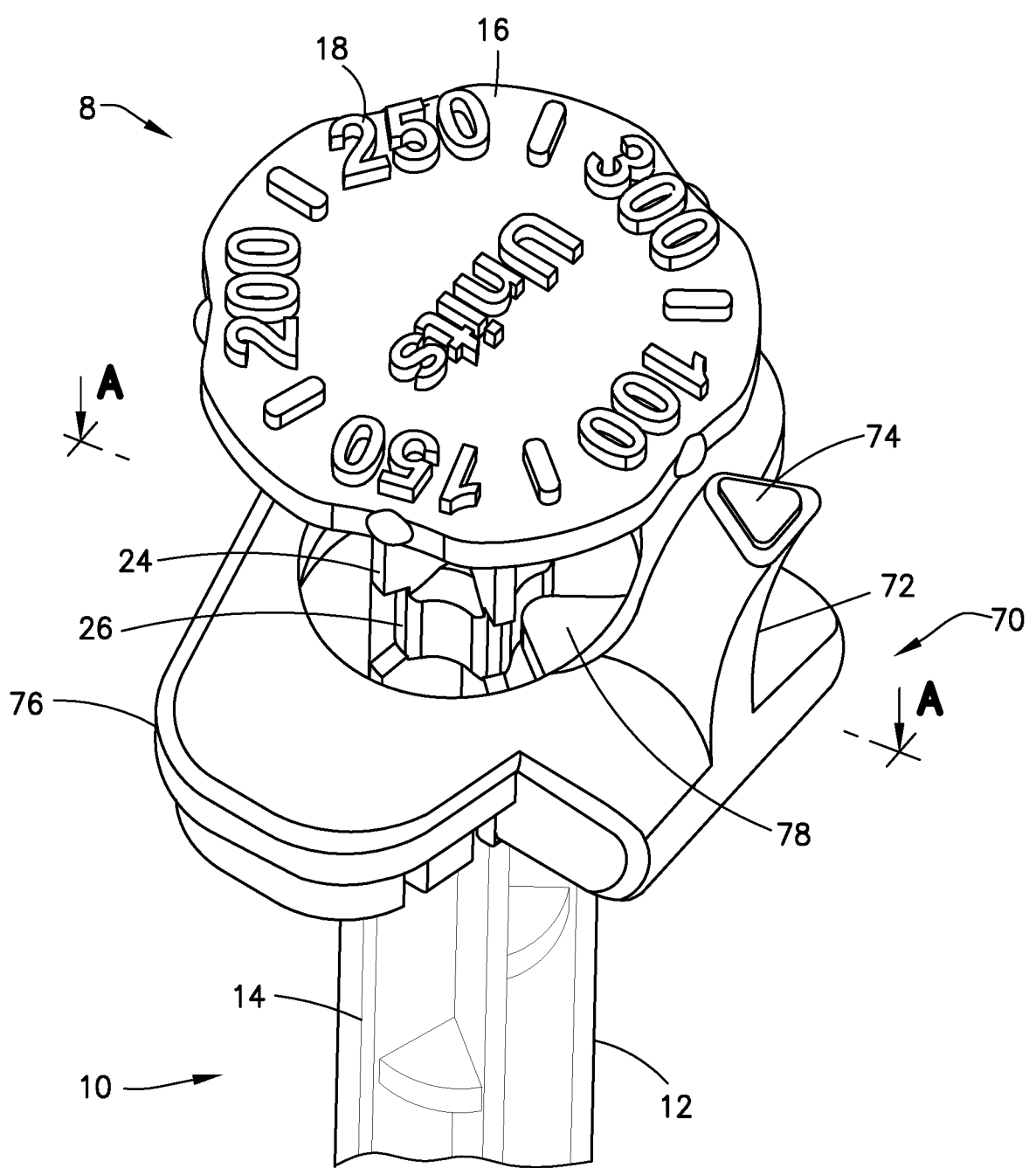
FIG. 6 illustrates a fourth exemplary embodiment of a right perspective view of a syringe assembly providing haptic feedback.
Figure 7:
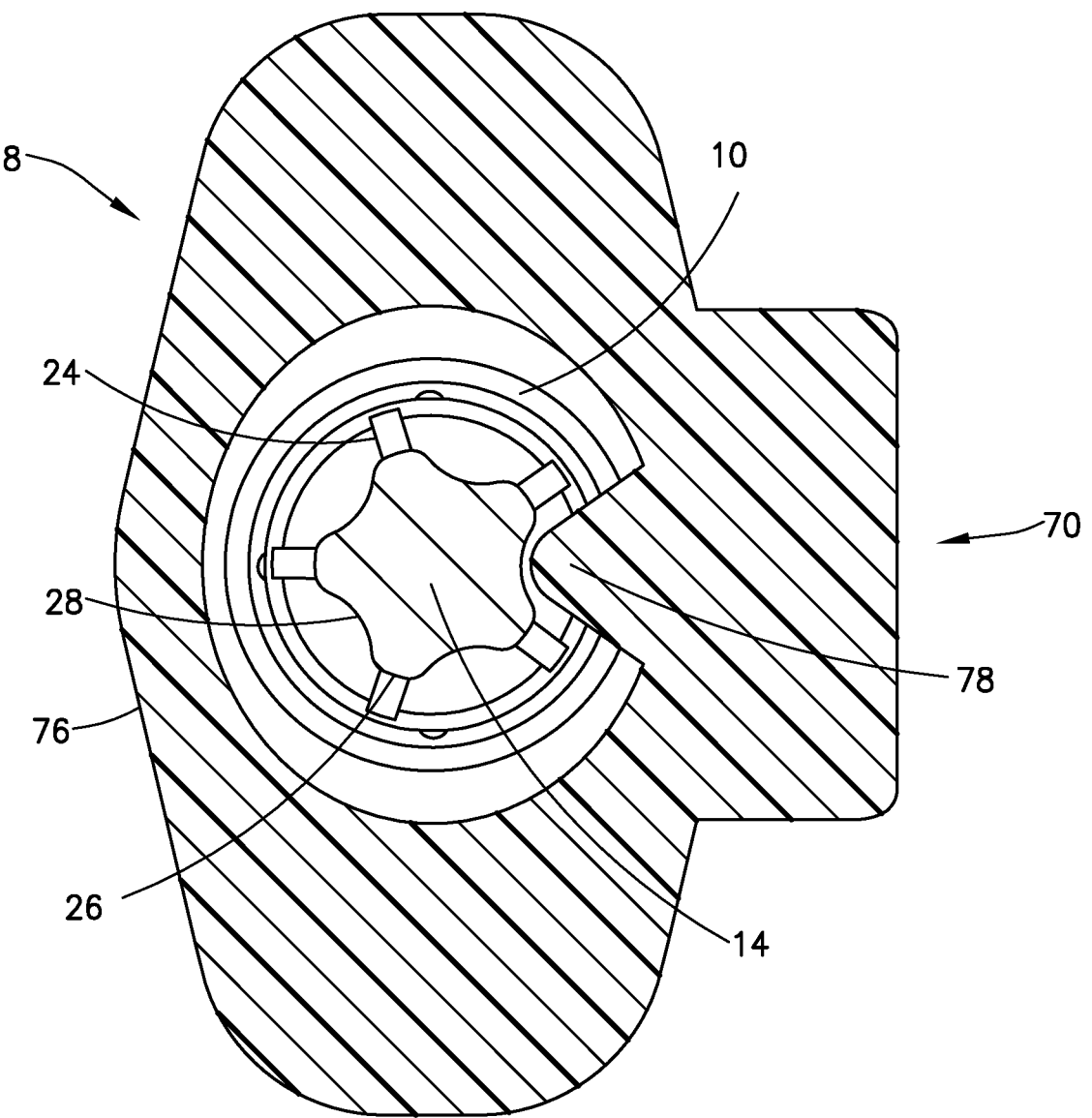
FIG. 7 is a cross-sectional view of the syringe assembly along line A-A of FIG. 6.

FIGS. 6 and 7 illustrate a syringe assembly 8 according to a fourth embodiment. This embodiment discloses the syringe 10 as similarly described above with the following modifications. This embodiment incorporates a dose selector 70 with the syringe 10 to advantageously provide haptic feedback to the user when setting a dose.

The plunger 14 of the syringe 10 is modified to cooperate with the dose selector 70. Specifically, the plunger 14 includes a plurality of axial ribs 24 extending along a length of the plunger 14. The axial ribs 24 provide stability and stiffness to the plunger 14. A curved indent 28 is disposed between each of the adjacent axial ribs 24.

FIG. 6 illustrates that a vertical portion of the plurality of axial ribs 24 includes a notch 26. A cross section of the plunger 14 at the notch 26 is illustrated in FIG. 7. The notch 26 advantageously provides a smooth raised surface around the plunger 14. The notch 26 also advantageously provides a continuous surface between the adjacent curved indents 28.

FIG. 6 further illustrates the dose selector 70 including an arm 72, a position indicator 74, a base 76 and a tab 78. The base 76 is fixed to and surrounds the barrel 12 of the syringe 10. The arm 72 extends upwardly from the base 76 and includes the position indicator 74 such as an arrowhead, for example, that indicates a set dose. The base 76 and the position indicator 74 are also similarly described above for various embodiments of the locking assembly.

The tab 78 is an inwardly extending member disposed on an inner surface of the base 76. The tab 78 cooperates with the plunger 14 and the notch 26. Specifically, the plunger 14 can only move vertically when the tab 78 is disposed between the axial ribs 24, in the curved indent 28 and outside of the notch 26 of the plunger 14. The user places the tab 78 at a vertical position of the plunger 14 where the notch 26 is located to rotate the plunger 14 and adjust the dosage.

When the user rotates the plunger 14 to set the dose, every time the tab 78 encounters the notch 26 of one of the axial ribs 24, a detent or force is advantageously provided. As illustrated in FIG. 7, this force or detent occurs because there is contact between the axial rib 24 and the tab 78 in the notch 26. This detent or force is the haptic feedback the user receives to indicate that the dosage is being changed. In this position, the plunger 14 is also locked to prevent vertical movement.

When the tab 78 is disposed between two of the axial ribs 24 as illustrated in FIG. 7, no detent or force is provided because there is no contact. That is, the tab 78 does not contact the curved indent 28. Accordingly, the user advantageously experiences alternate pressures (haptic feedback) when rotating between dose setting positions.

Figure 8:
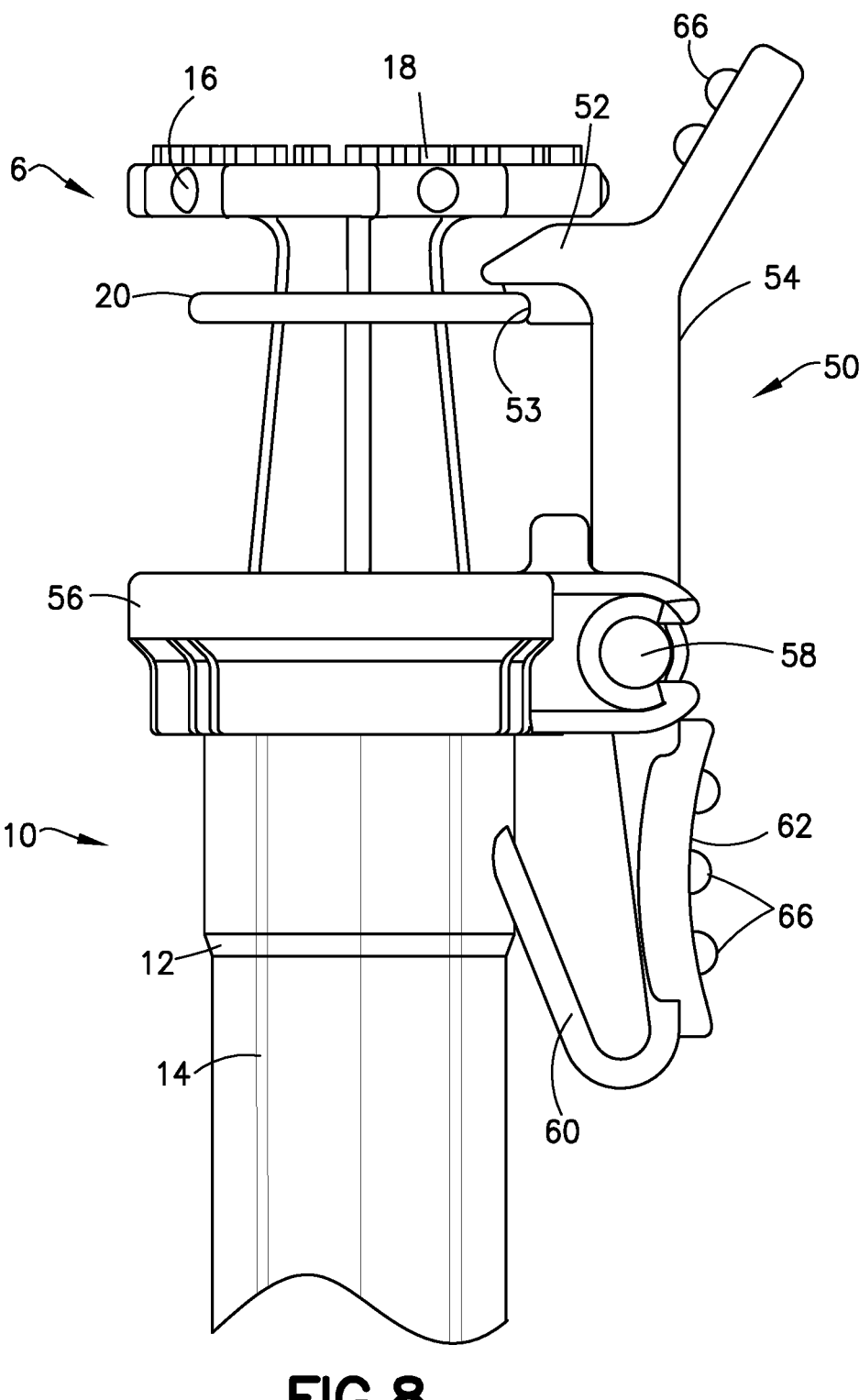
FIG. 8 illustrates a fifth exemplary embodiment of a side elevation view of a syringe assembly engaging the plunger head platform.

FIG. 8 illustrates a syringe assembly 9 according to a fifth embodiment. This embodiment also discloses the syringe 10 and the locking assembly 50 as similarly described above with the following modifications. Specifically, the plunger head platform 20 includes a rounded circumferential surface that the hook 52 engages. More specifically, the hook 52 includes a hook indent 53 that is contoured to engage and receive the rounded circumferential surface of the plunger head platform 20. Such a configuration advantageously provides a more secure and smooth engagement of the hook 52 to the platform 20 when the locking assembly 50 is in the locked position.

Figure 9:
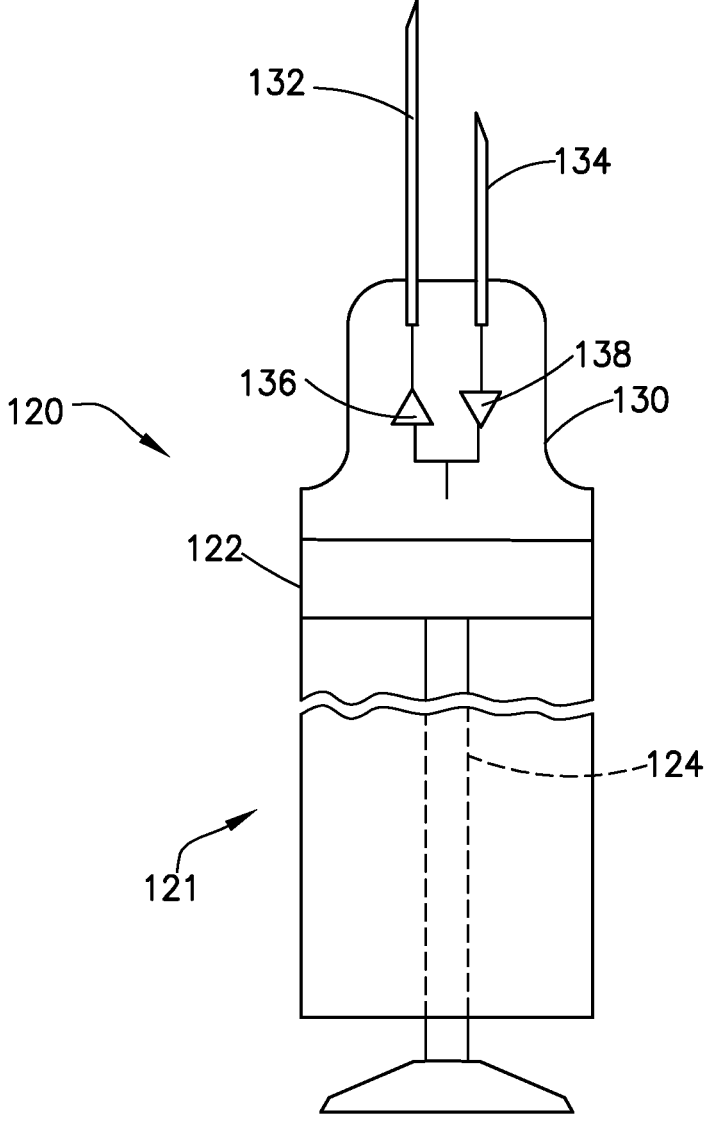
FIG. 9 illustrates a sixth exemplary embodiment of a cross-sectional view of a fluid transfer device engaged to a syringe.
Figure 10:
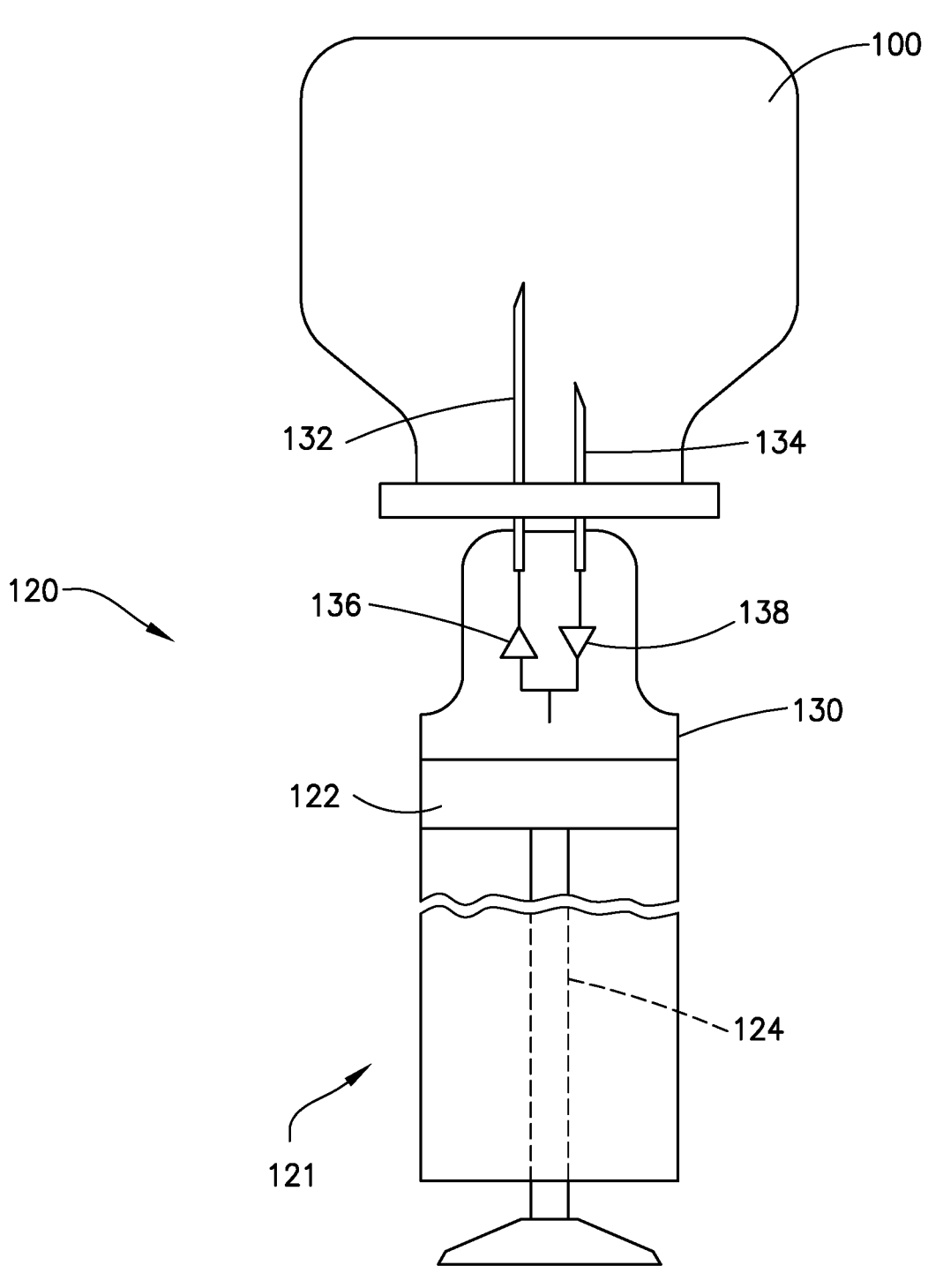
FIG. 10 is a cross-sectional view of the fluid transfer device of FIG. 9 engaged to a vial.
Figure 11:
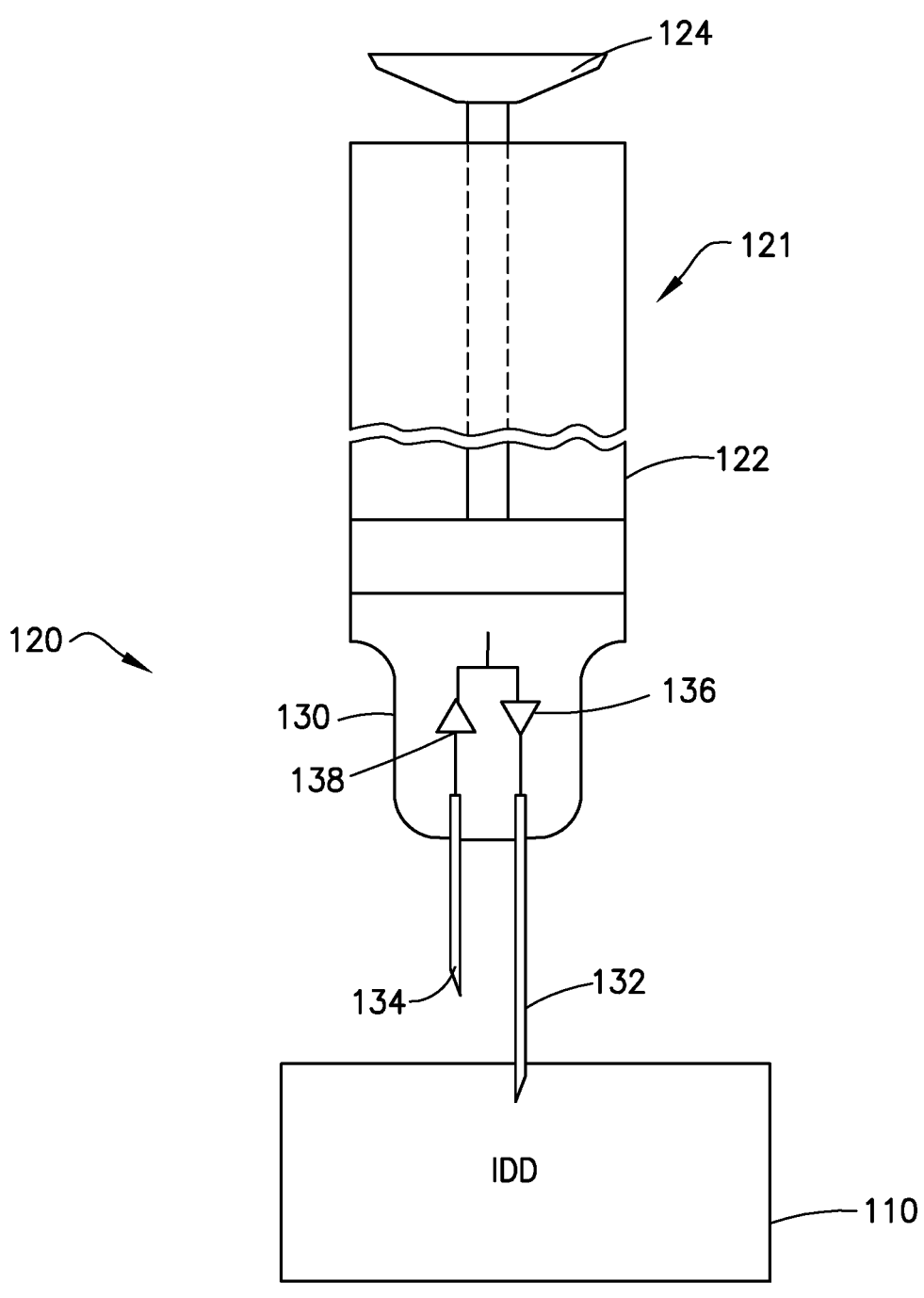
FIG. 11 is a cross-sectional view of the fluid transfer device of FIG. 9 engaged to an insulin delivery device.

FIGS. 9-11 illustrate a cross-sectional view of a fluid transfer device 120 attached to a syringe 121 according to a fifth embodiment. FIG. 10 illustrates the fluid transfer device 120 engaged to a vial 100 to receive medicament. FIG. 11 illustrates the fluid transfer device 120 engaged to an insulin delivery device (IDD) 110 to transfer medicament. Further details of the fluid transfer device 120 are provided below.

The syringe 121 is commonly understood by one skilled in the art and includes, for example, a barrel 122 that carries the medicament and a plunger 124 disposed in the barrel 122 to draw and dispense the medicament. The syringe 121 is configured to engage a vial adapter 130 of the fluid transfer device 120 to establish fluid communication. In an alternate embodiment, the fluid transfer device 120 includes the barrel 122 and the plunger 124 that are in fluid communication with the vial adapter 130.

The vial adapter 130 includes a first needle cannula 132, a second needle cannula 134, a first one-way valve 136 and a second one-way valve 138. The first needle cannula 132 is used for transferring the medicament from the barrel 122 into the insulin delivery device 110 as illustrated in FIG. 11. The second needle cannula 134 is used to receive the medicament from the vial 100 as illustrated in FIG. 10.

The first needle cannula 132 is advantageously longer than the second needle cannula 134 so that only the first needle cannula 132 engages the insulin delivery device 110. As illustrated in FIG. 11, the second needle cannula 132 is too short to engage the insulin delivery device 110.

On the other hand, the second needle cannula 134 is advantageously shorter than the first needle cannula 132 to receive more of the medicament from the vial 100. FIG. 10 illustrates that both the first and second needle cannulas 132, 134 are disposed in the vial 100. However, a distal end of the second needle cannula 134 is closer to a bottom portion of the vial 100. As the medicament exits the vial 100, the associated fluid level decreases in the vial 100. Having a short needle cannula 134 advantageously optimizes the amount of medicament that can be removed from the vial 100.

The first one-way valve 136 controls medicament flow through the first needle cannula 132 such that the medicament in the barrel 122 can only exit through the first needle cannula 132. That is, the first one-way valve 136 does not allow the first needle cannula 132 to receive the medicament into the barrel 122.

On the other hand, the second one-way valve 138 controls medicament flow through the second needle cannula 134 such that the medicament can only enter through the second needle cannula 134 to fill the barrel 122. Conversely, the second one-way valve 138 does not allow the second needle cannula 134 to dispense the medicament from the barrel 122.

The fluid transfer device 120 of this embodiment provides an alternate means to prevent backflow of the medicament from the insulin delivery device 110 into the syringe 121. To achieve this benefit, the fluid transfer device 120 advantageously provides separate fluid paths without the use of a plunger locking mechanism and without the need to manually hold down a syringe plunger after fluid delivery.

Figure 12:
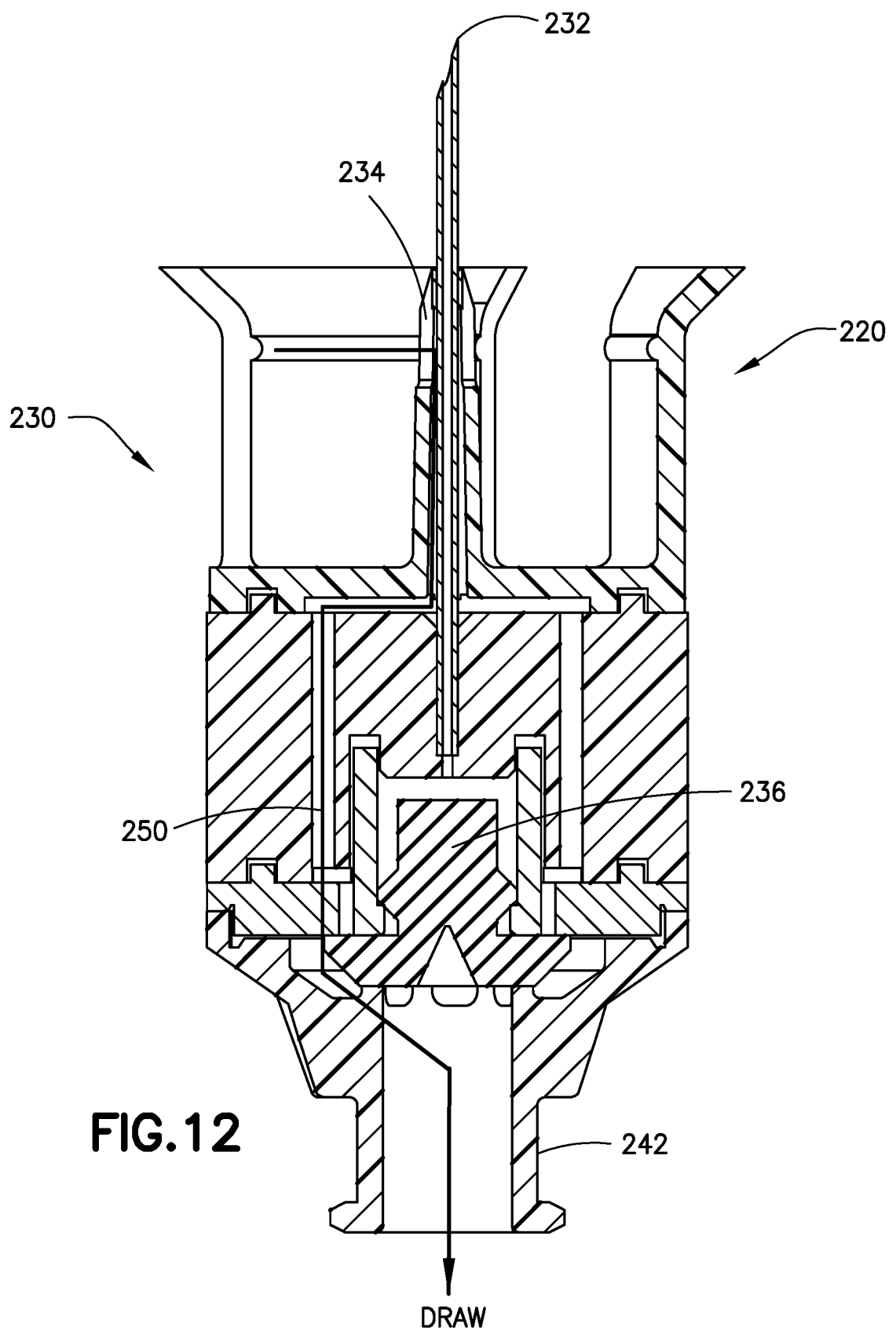
FIG. 12 illustrates a seventh exemplary embodiment of a cross-sectional view of a fluid transfer device drawing medicament.
Figure 13:
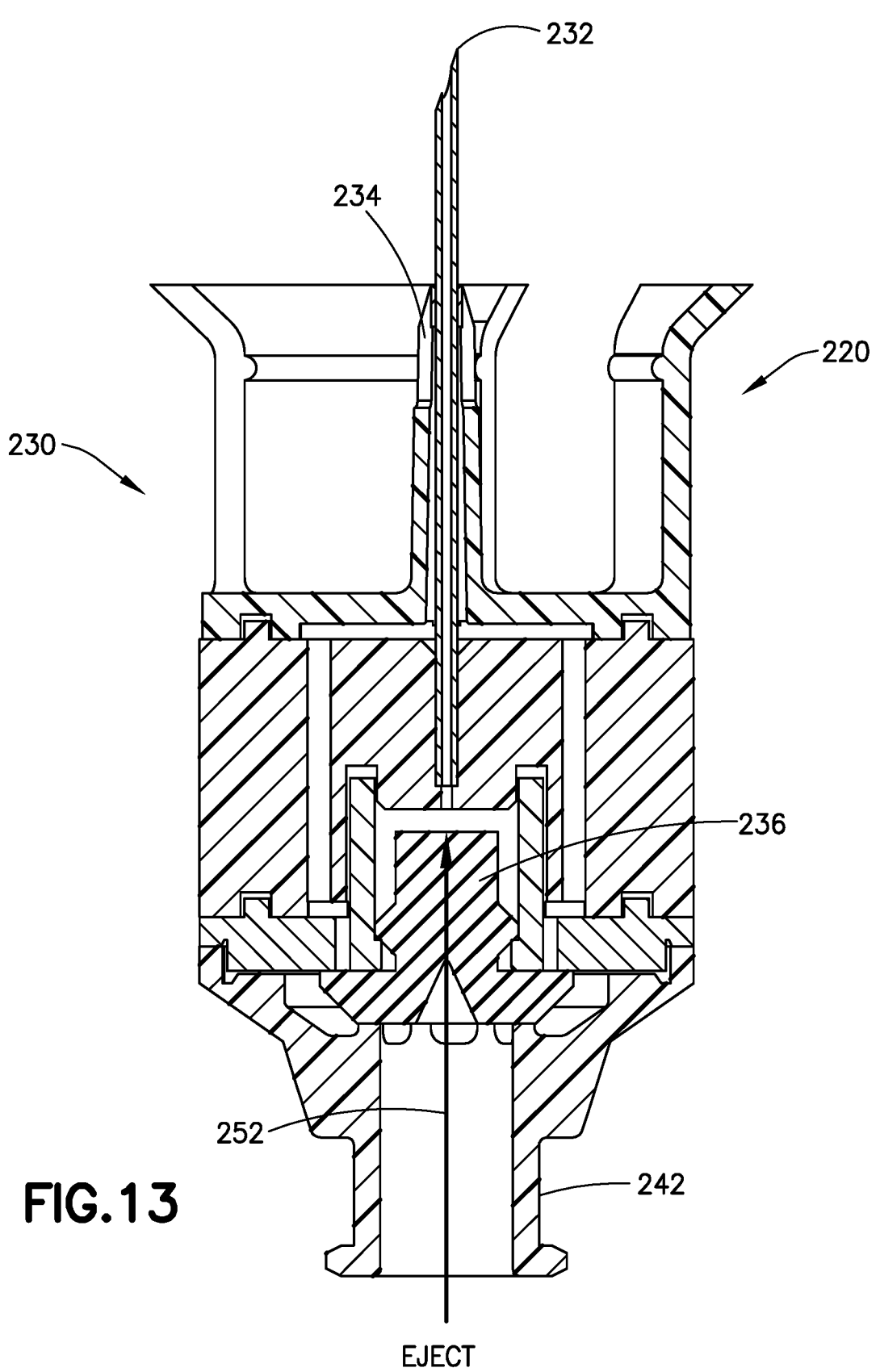
FIG. 13 is a cross-sectional view of the fluid transfer device of FIG. 12 shown expelling the medicament.
Figure 14:
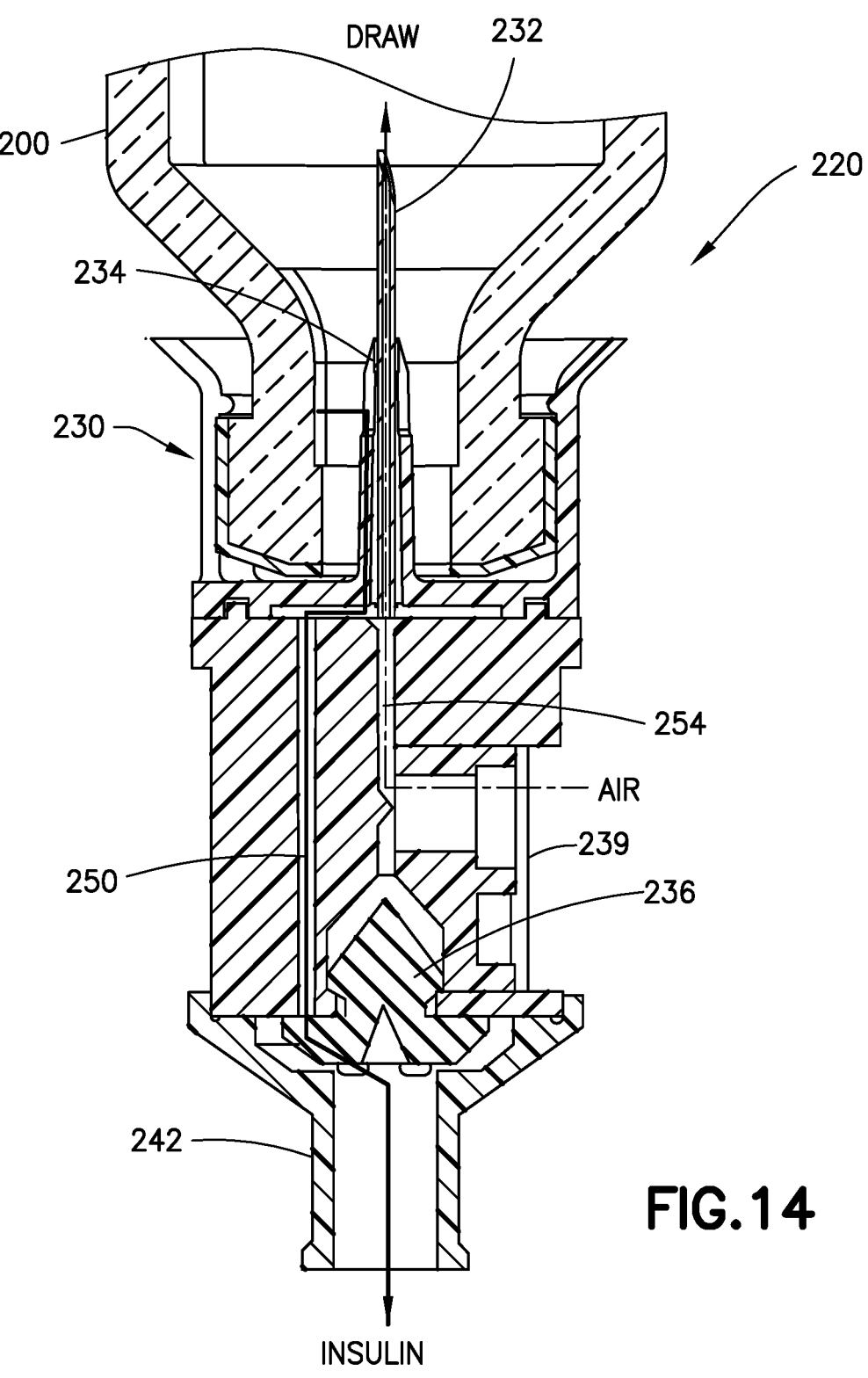
FIG. 14 is a cross-sectional view of the fluid transfer device of FIG. 12 shown drawing the medicament and providing an air vent passage.

FIGS. 12-15 illustrate a cross-sectional view of a fluid transfer device 220 according to a sixth embodiment. The fluid transfer device 220 includes a vial adapter 230, a first needle cannula 232, a second needle cannula 234, a two-way valve 236, a vent membrane 239 and a syringe adapter 242. FIG. 14 illustrates that the vial adapter 230 is engaged to a vial 200, preferably via a snap lock engagement, although other means are contemplated herein. The syringe adapter 242 is configured to engage a syringe (not shown), preferably via a luer lock, although other means are contemplated herein.

Figure 15:
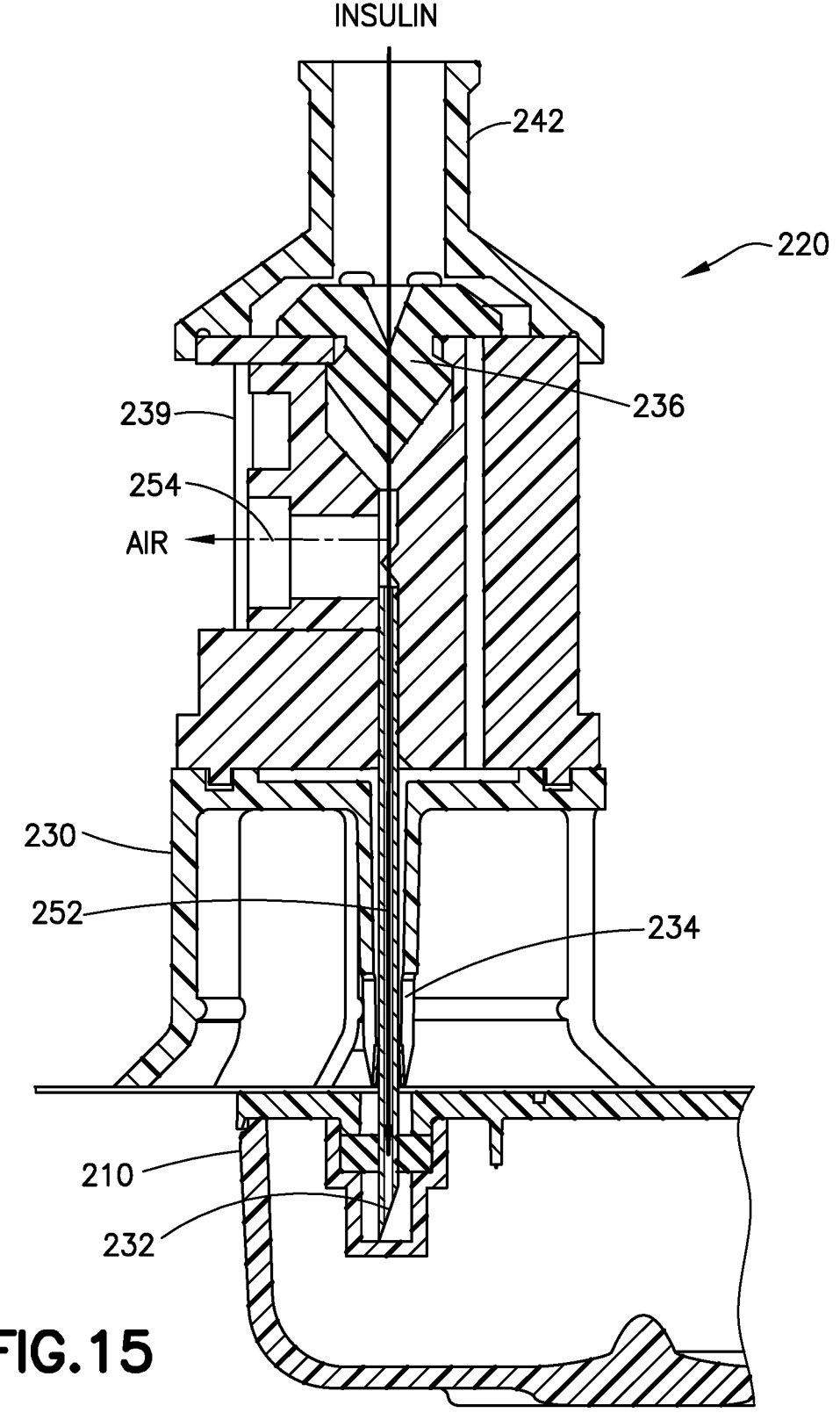
FIG. 15 is a cross-sectional view of the fluid transfer device of FIG. 12 shown expelling the medicament and providing an air vent passage.

As similarly described above, the first needle cannula 232 is used for transferring the medicament from the syringe into the insulin delivery device 210 as illustrated in FIG. 15. The second needle cannula 234 is used to receive the medicament from the vial 200 as illustrated in FIG. 14.

The first needle cannula 232 is advantageously longer than the second needle cannula 234 so that only the first needle cannula 232 engages the insulin delivery device 210. A bottom surface of the vial adapter 230 advantageously controls the insertion depth of the first needle cannula 232 in the insulin delivery device 210. As illustrated in FIG. 15, the second needle cannula 232 is too short to engage the insulin delivery device 210. Specifically, the second needle cannula 232 does not extend beyond the bottom surface of the vial adapter 230 to advantageously ensure that no fluid communication to the insulin delivery device 210 takes place.

On the other hand, the second needle cannula 234 is advantageously shorter than the first needle cannula 232 to receive more of the medicament from the vial 200. FIG. 14 illustrates that a distal end of the second needle cannula 234 is closer to a bottom portion of the vial 200. As the medicament exits the vial 200, the associated fluid level decreases in the vial 200. Having a short second needle cannula 234 optimizes the amount of medicament that is removed from the vial 200. A depth of a cavity in the vial adapter 230 that engages the vial 200 advantageously controls the insertion depth of the second needle cannula 234.

Further, the first needle cannula 232 is advantageously disposed within the second needle cannula 234. Such a configuration optimizes space, provides a simple design and continues to provide different fluid paths as described in more detail below.

The two-way valve 236 is preferably a combination duckbill and umbrella valve. However, other combination of valves can be used to achieve the functional benefits described herein. The two-way valve 236 controls medicament flow through the first needle cannula 232 such that the medicament in the syringe can only exit through the first needle cannula 232. That is, the two-way valve 236 does not allow the first needle cannula 232 to receive the medicament into the syringe.

The two-way valve 236 also controls medicament flow through the second needle cannula 234 such that the medicament can only enter through the second needle cannula 234 to fill the syringe. Similarly, the two-way valve 236 does not allow the second needle cannula 234 to dispense the medicament from the syringe.

In view of the above, the two-way valve 236 advantageously controls the transfer of the medicament. However, the two-way valve 236 does not control the exchange of air. Further explanation of an airflow path 254 in the fluid transfer device 220 is described below.

FIGS. 12-15 also illustrate a vent membrane 239 connecting to the airflow path 254, as well as a medicament entrance path 250 and a medicament exit path 252. FIG. 12 illustrates the syringe being filled with the medicament. Specifically, the medicament entrance path 250 is described in a manner where the medicament enters a distal end of the second needle cannula 234, routed in a path offset from the centerline of the vial adapter 230 to the two-way valve 236 and ultimately enters into the syringe adapter 242 to fill the syringe.

FIG. 14 illustrates the medicament entrance path 250 when the vial adapter 230 is engaged to the vial 200. The vent membrane 239 cooperates with the transfer of the medicament from the vial 200 to the syringe and is located upstream from the two-way valve 236.

Specifically, when the medicament exits the vial 200, air advantageously enters into the vial 200 via the airflow path 254 and the vent membrane 239. The airflow path 254 includes a path upstream from the two-way valve 236 and through the first needle cannula 232. In this manner, there is no vacuum created in the vial 200 and the pressure in the vial 200 is equalized with the environmental pressure.

FIGS. 13 and 15 illustrate the medicament exit path 252 that allows the medicament to exit the syringe and enter the insulin delivery device 210. The medicament exit path 252 travels through the two-way valve 236, through a centerline of the fluid transfer device 220, and through the first needle cannula 232 before ultimately entering into the insulin delivery device 210.

Meanwhile, the same airflow path 254 through the first needle cannula 232 and the vent membrane 239 as described above is used to remove air from the insulin delivery device 220. Advantageously, there is no vacuum created in the insulin delivery device 220 and the pressure in the insulin delivery device 220 is equalized with the environmental pressure.

The fluid transfer device 220 of this embodiment provides an alternate means to prevent backflow of the medicament from the insulin delivery device 210 into the syringe. To achieve this benefit, the fluid transfer device 220 advantageously provides separate fluid and air paths without the use of a plunger locking mechanism and without the need to manually hold down a syringe plunger after fluid delivery.

The foregoing detailed description of the certain exemplary embodiments has been provided for explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. In addition, any of the embodiments, features and/or elements disclosed herein may be combined with one another to form various additional combinations not specifically disclosed, as long as the embodiments, features and/or elements being combined do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges around and including the given value, for example, general tolerances associated with manufacturing, assembly, and use of the described embodiments.

The invention claimed is:

1. A syringe assembly that locks a syringe to prevent backflow of medicament, the syringe assembly comprising:
   a syringe, including:
      a barrel configured to carry the medicament;
      a plunger that communicates with the barrel; and
      a plunger head disposed on a proximal end of the plunger; and
   a locking assembly disposed around the barrel, the locking assembly including a hook configured to engage the plunger head;
   wherein the locking assembly prevents the plunger from moving away from the barrel to draw the medicament into the barrel.

2. The syringe assembly of claim 1, wherein the plunger head includes a dial dose to indicate a dose setting.

3. The syringe assembly of claim 1, wherein: the locking assembly includes: a depressible button and a spring member connected to the hook, wherein the depressible button controls engagement and disengagement between the hook and the plunger head.

4. The syringe assembly of claim 3, wherein:
the locking assembly further includes:
  a base engaged to the barrel;
  an arm that connects the hook to the depressible button
    and the spring member; and
  a shaft that connects the arm to the base.

5. The syringe assembly of claim 4, wherein the shaft
allows the arm to rotate to control engagement and disen-
gagement between the hook and the plunger head.

6. The syringe assembly of claim 4, wherein:
the spring member contacts the barrel and is disposed on
  one side surface of the arm while the button is disposed
  on an opposing side surface of the arm;
when the button is in a free state, the spring member is
  compressed at a first compression force and the hook is
  engaged to the plunger head;
when the button is depressed, the spring member is
  compressed at a second compression force and the
  hook is disengaged from the plunger head; and
the second compression force is greater than the first
  compression force.

7. The syringe assembly of claim 3, wherein:
the plunger head further includes a platform disposed
  distally from a top surface of the plunger head; and
the hook is configured to engage the plunger between the
  top surface of the plunger head and the platform to lock
  the plunger.

8. The syringe assembly of claim 7, wherein the hook
includes an indent feature that engages and disengages the
platform to secure engagement.

9. The syringe assembly of claim 3, wherein the hook
includes one of protrusions and a position indicator to aid in
handling and dose setting.

10. The syringe assembly of claim 1, wherein the hook is
configured to engage a proximal surface of the plunger head.

11. The syringe assembly of claim 10, wherein the hook
engages the plunger head after the medicament is dispensed
from the barrel of the syringe.

12. The syringe assembly of claim 1, wherein the locking
assembly includes a depressible button and a spring member
connected to the hook.

* * * * *